US00PP32235P2

(12) United States Plant Patent
Bradford et al.

(10) Patent No.: US PP32,235 P2
(45) Date of Patent: Sep. 29, 2020

(54) CHERRY TREE NAMED 'JONRED I'

(50) Latin Name: *Prunus avium*
Varietal Denomination: Jonred I

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 16/602,915

(22) Filed: Dec. 23, 2019

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 6/7445; A01H 5/08
See application file for complete search history.

(56) References Cited

U.S. PATENT DOCUMENTS

PP12,859 P2 8/2002 Bradford

*Primary Examiner* — Keith O. Robinson

(57) ABSTRACT

The present invention relates to a cherry tree, *Prunus avium*, and more particularly to a new and distinct variety broadly characterized by a medium size, moderately vigorous, hardy, self-unfruitful, and productive tree. The fruit matures under the ecological conditions described in mid May, with first picking on May 15, 2019. The fruit is uniformly large in size, very sweet in flavor, oblate in shape, clingstone in type, very firm in texture, dark red in flesh color, very dark red in skin color, and has a medium length stem that is strongly attached to the fruit.

1 Drawing Sheet

Botanical classification: *Prunus avium.*
Varietal denomination: 'JONRED I'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of cherry tree, which has been denominated varietally as 'Jonred I'.

During a typical blooming season we isolate as seed parents individual cherry trees by covering them with screen houses. A hive of bees is placed inside each such house, and bouquets to provide pollen from different cherry trees are placed in buckets near the trees approximately every two days for the duration of the bloom. During 2008 one such house containing 'Glenred' (U.S. Plant Pat. No. 12,859) cherry tree was crossed by us in this manner. To pollinate this cherry, we selected bouquets from several sources of cherry trees without keeping specific written details. Upon reaching maturity the fruit from this cherry tree was harvested and the seeds were removed, cracked, stratified and germinated as a group with the label 'Glenred House'. They were grown as seedlings on their own root in our greenhouse, and upon reaching dormancy transplanted to a cultivated area of our experimental orchard located near Le Grand, Calif. in Merced County (San Joaquin Valley). During the summer of 2013 the claimed variety was selected by us as a single tree from the group of seedlings described above. Subsequent to origination of the present variety of cherry tree, we asexually reproduced it by budding and grafting in the experimental orchard described above, and such reproductions were true to the original tree in all respects. The reproduction of the variety included the use of 'Colt' (unpatented) rootstock, upon which the present variety was compatible and true to type.

The present variety is most similar to its seed parent, 'Glenred' (U.S. Plant Pat. No. 12,859) cherry, by having a moderately vigorous tree, by blooming heavy, by being self-unfruitful, by having oval to reniform leaf glands, by being productive, and by producing medium to large cherries that are dark red in skin color, dark red in flesh color, oblate in shape, and fairly crack resistant, but is distinguished therefrom by blooming about six days later and by producing cherries that ripen about five days earlier, that are firmer in texture, that are sweeter in flavor, and that have a stronger stem attachment.

SUMMARY OF VARIETY

In summary, the present cherry variety is characterized by a medium size, moderately vigorous, hardy, self-unfruitful, and productive tree. The fruit matures under the ecological conditions described in mid May, with first picking on May 15, 2019. The fruit is uniformly large in size, very sweet in flavor, oblate in shape, clingstone in type, very firm in texture, dark red in flesh color, very dark red in skin color, and has a medium length stem that is strongly attached to the fruit.

DRAWING

The accompanying photograph displays four whole fruits with the stems attached, two whole fruits detached from the stems to exhibit the skin color and form, a sectioned fruit to reveal the flesh, fibers, and stone, two insets depicting flowers and buds, a typical tip shoot, and several leaves, all typical of the subject variety.

POMOLOGICAL CHARACTERISTICS

Referring now more specifically to the pomological characteristics of this new and distinct variety of cherry tree, the following has been observed under the ecological conditions prevailing near Le Grand, Merced County (San Joaquin Valley), Calif., and was developed at the state of firm ripe on May 19, 2019, on the original tree during its eighth growing season. All major color code designations are by reference to the Inter-Society Color Council, National Bureau of Standards. Common color names are also used occasionally.

PARENTAGE

Seed parent: 'Glenred' cherry (U.S. Plant Pat. No. 12,859).
Pollen parent: Unknown.

TREE

Size: Medium, maintained to a height of 10' [3.05 m.] and a spread of 8' [2.44 m.] after eleven growing seasons utilizing typical pruning.

Vigor: Moderately vigorous, responding typically to irrigation and fertilization. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive.

Fertility: Self-unfruitful, must be cross pollinated by another early to mid seasonal blooming cherry variety, such as 'Arvin Glen' (U.S. Plant Pat. No. 23,721).

Bearing: Fairly regular, dependent upon seasonal blooming weather.

Leaf bud burst: Toward the end of flowering.

Trunk:

*Size*.—Medium, reaching a maximum diameter of 4½" [114.3 mm.] after the eleventh growing season.

*Texture*.—Smooth.

*Bark color*.—A Grayish yellowish brown [80. gy.yBr] and Moderate yellowish brown [77. m.yBr] variegation with Strong yellowish brown [74. s.yBr] crevices present.

*Lenticels*.—Approximate Number Per Square Inch: 10. Color: Brownish orange [54. brO]. Average Size: Length is ⅜" [9.5 mm.] with a width of 1/16" [1.6 mm.]. Shape: Eye-shaped, elongated.

Branches:

*Size*.—Medium, diameter of main scaffold measured 12" above the crotch is 1¾" [44.5 mm.], diameter of limb is 1¼" [31.8 mm.] measured 12" above the first fork.

*Texture*.—Smooth on first and second year wood, increasing roughness with age.

*Color*.—1st Year Wood topside: Grayish red [19. gy.R]. 1st Year Wood underside: Brilliant yellow green [116. brill.YG]. 2nd Year Wood: A Moderate brown [58. m.Br] and Grayish brown [61. gy.Br] variegation.

*Lenticels*.—Number Per Square Inch: About 15 on second year wood. Color: Deep orange [51. deep O]. Average Size: Length is ⅛" [3.2 mm.] and width is 1/32" [0.8 mm.]. Shape: Eye-shaped, elongated.

Leaves:

*Size*.—Medium. Average Length: 5¼" [133.4 mm.]. Average Width: 2 3/16" [55.6 mm.].

*Arrangement*.—Alternate.

*Thickness*.—Medium.

*Form*.—Elliptical.

*Apex*.—Acuminate.

*Base*.—Acute.

*Surface*.—Smooth on both sides.

*Color*.—Dorsal Surface: Moderate olive green [125. m.OlG]. Ventral Surface: Moderate yellow green [120. m.YG].

*Red midvein*.—Absent.

*Margin*.—Finely serrate.

*Venation*.—Pinnately net veined.

*Vein color*.—Strong yellow green [117. s.YG].

*Petiole*.—Average Length: 1 9/16" [39.7 mm.]. Average Thickness: 1/16" [1.6 mm.]. Color: Grayish red [19. gy.R] on the topside, Strong yellow green [117. s.YG] underneath.

*Stipules*.—Number: 2 per leaf, up to 6 per growing tip. Average Length: ¼" [6.4 mm.]. Color: Brilliant yellow green [116. brill.YG] turning Grayish red [19. gy.R] with age.

*Glands*.—Number: Usually 2-3 per leaf. Position: Mostly alternate. Size: Large, 1/16" [1.6 mm.] in diameter. Form: Reniform to oval. Color: Light orange yellow [70. l.OY] with a Strong red [12. s.R] center.

*Leaf buds*.—Pointed.

Flower buds:

*Hardiness*.—Hardy with respect to central California blooming season.

*Diameter*.—Typically 5/16" [7.9 mm.] 3 days before bloom.

*Length*.—Typically ⅝" [15.9 mm.] 3 days before bloom.

*Form*.—Not appressed.

*Surface*.—Very slightly pubescent.

*Tip color*.—White [263. White].

Flowers: Perfect, complete, perigynous, usually a single pistil, typically about twenty stamens, five sepals and petal locations alternately positioned.

*Average flower diameter*.—1⅝" [41.3 mm.].

*Average flower depth*.—½" [12.7 mm.] when fully open.

*Average pedicel length*.—7/16" [11.1 mm.].

*Number of petals*.—Usually five, a few extra petal fragments typically observed.

*Petal arrangement*.—Overlapping.

*Petal shape*.—Circular to slightly obovate.

*Petal margin*.—Somewhat wavy.

*Average petal diameter*.—11/16" [17.5 mm.].

*Average petal length*.—11/16" [17.5 mm.].

*Petal apex*.—Rounded.

*Petal base*.—Obtuse.

*Petal color*.—White [263. White] on both sides.

*Anther color*.—Light orange yellow [70. l.OY].

*Stigma color*.—Vivid greenish yellow [97. v.gY].
*Stigma position*.—Typically located about 1/16" [1.6 mm.] above the nearby anthers.
*Stamen position*.—Typically located about 1/32" [0.8 mm.] below the petals.
*Ovary*.—Non-pubescent.
*Sepal color*.—Grayish red [19. gy.R] over Brilliant yellow green [116. brill.YG] on the outer surface. The inner surface is Light yellow green [119. l.YG].
*Sepal outer surface*.—Slightly pubescent.
*Sepal length*.—3/8" [9.5 mm.].
*Sepal width*.—3/16" [4.8 mm.].
*Sepal apex*.—Elliptical to match the sepal length and width.
*Sepal margin*.—Fairly smooth.
*Average pistil length*.—11/16" [17.5 mm.].
*Average stamen length*.—9/16" [14.3 mm.].
*Fragrance*.—Moderate.
*Pollen production*.—Moderate.
*Pollen color*.—Strong yellow [84. s.Y].
*Bloom density*.—Heavy.
Blooming period.—Medium, blooms six days later than 'Glenred' (U.S. Plant Pat. No. 12,859) cherry.
*Onset of bloom*.—One percent on Mar. 22, 2019.
*Date of full bloom*.—Mar. 31, 2019.
*Duration of bloom*.—One to two weeks, dependent on ambient temperature.
*Number per cluster*.—Usually 2 to 6, 3 average.

FRUIT

Maturity when described: Firm ripe, May 19, 2019.
Date of first picking: May 15, 2019.
Date of last picking: May 25, 2019.
Size: Uniform, large.
*Average diameter axially*.—15/16" [23.8 mm.].
*Average diameter across cheek plane*.—1¼" [31.8 mm.].
*Average diameter across suture plane*.—1" [25.4 mm.].
*Typical weight*.—0.45 ounces [12.8 grams].
Form: Uniform, symmetrical, oblate.
*Axial view form*.—Elliptical.
*Suture plane form*.—Oval.
*Cheek plane form*.—Oblate.
Suture: A faint Reddish black [24. rBlack] line located in a very shallow trough extending from the base to the pistil point.
Ventral surface: Rounded, lipped toward the apex.
Lips: Equal.
Cavity: Flaring, rounded, suture showing on one side.
*Depth*.—⅛" [3.2 mm.].
*Breadth*.—11/16" [17.5 mm.].
Base: Truncate, slightly cordate if viewed parallel to the suture.
Apex: Rounded to somewhat truncate.
Pistil point: A Light reddish brown [42. l.rBr] dot.
Stem: Medium to long, thick.
*Average length*.—1½" [38.1 mm.].
*Average width*.—3/32" [2.4 mm.].
*Attachment*.—Strong.
Skin:
*Thickness*.—Medium.
*Surface*.—Smooth.
*Tenacity*.—Tenacious to the flesh.
*Astringency*.—Moderate.
*Tendency to crack*.—None observed.
*Color*.—Blackish red [21. blackish R] smoothly blending to a Very dark red [17. v.d.R] background.
Flesh:
*Color*.—Very deep red [14. v.deep R] becoming Very dark red [17. v.d.R] next to the stone with Light orange yellow [70. l.OY] fibers throughout.
*Surface of pit cavity*.—Covered with Very dark red [17. v.d.R] fibers.
*Amygdalin*.—Moderate.
*Juice*.—Abundant, rich.
*Juice color*.—Very dark red [17. v.d.R].
*Texture*.—Very firm, crisp.
*Fibers*.—Abundant, fine.
*Ripens*.—Fairly evenly, slightly earlier at the shoulder.
*Flavor*.—A very tasty blend of acid and sugar, typically 24 brix.
*Aroma*.—Wanting.
*Eating quality*.—Excellent.

STONE

Type: Clingstone.
Form: Oval.
Hilum: Narrow, oblong.
Base: Rounded.
Apex: Acute.
Sides: Fairly equal.
Surface: Fairly smooth.
External color of stone: Strong yellowish brown [74. s.yBr].
Pit wall color when cracked: Pale orange yellow [73. p.OY].
Cavity surface color: Light orange yellow [70. l.OY].
Average pit wall thickness: 1/16" [1.6 mm.].
Average width: 7/16" [11.1 mm.].
Average length: ½" [12.7 mm.].
Average breadth: ⅜" [9.5 mm.].
Tendency to split: None observed.
Kernel:
*Form*.—Oval.
*Skin color*.—Yellowish white [92. yWhite] when first removed.
*Pellicle color*.—Strong yellowish brown [74. s.yBr].
*Taste*.—Bitter.
*Viable*.—Yes.
*Average width*.—3/16" [4.8 mm.].
*Average length*.—¼" [6.4 mm.].
*Amygdalin*.—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: Not tested.
Resistance to diseases: Not tested.

OTHER NOTES

Although the new variety of cherry tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of cherry tree, substantially as illustrated and described, that is most similar to its seed parent, 'Glenred' (U.S. Plant Pat. No. 12,859) cherry, by having a moderately vigorous tree, by blooming heavy, by being self-unfruitful, by having oval to reniform leaf glands, by being productive, and by producing medium to large cherries that are dark red in skin color, dark red in flesh color, oblate in shape, and fairly crack resistant, but is distinguished therefrom by blooming about six days later and by producing cherries that ripen about five days earlier, that are firmer in texture, that are sweeter in flavor, and that have a stronger stem attachment.

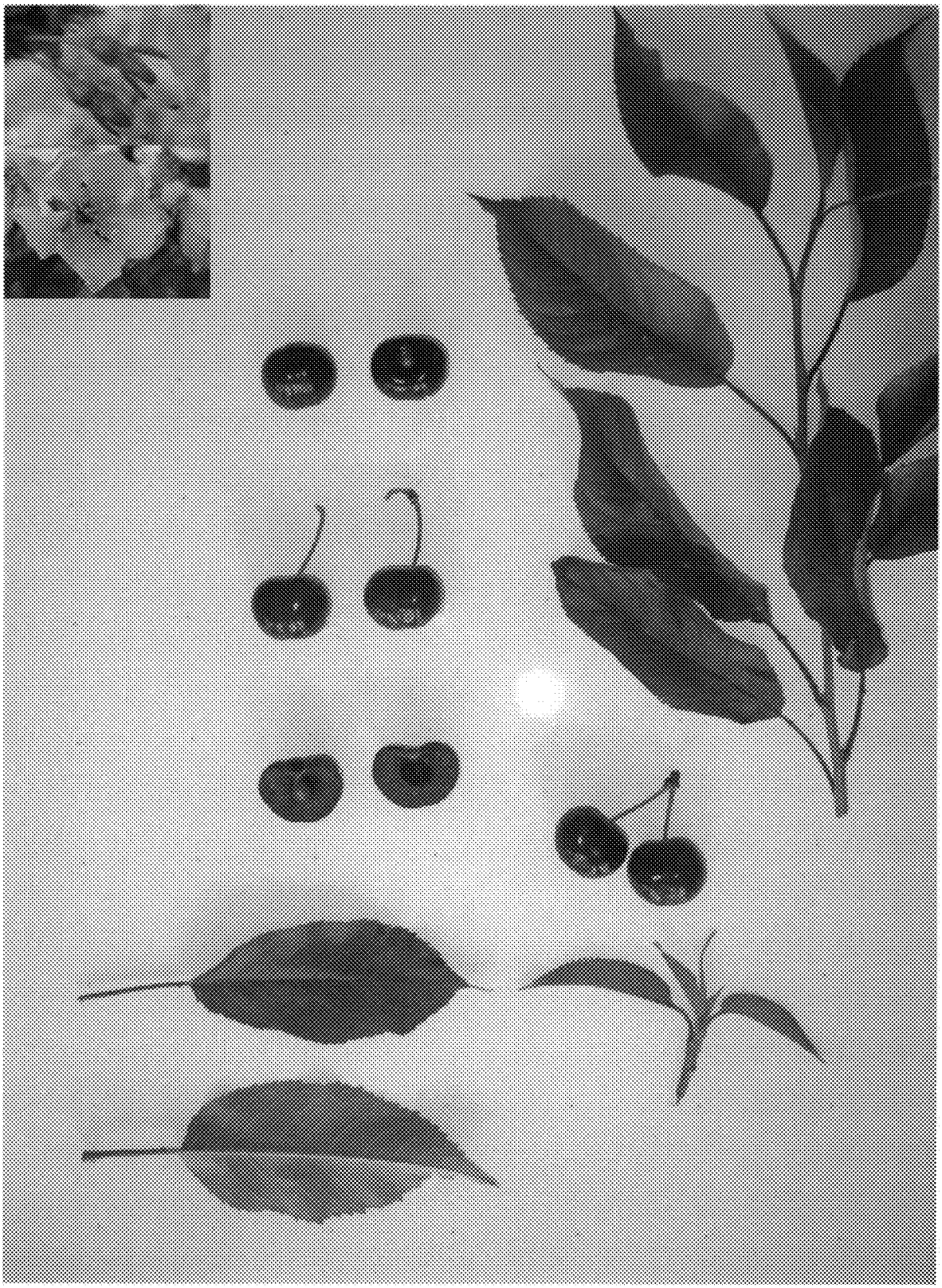

* * * * *